(12) United States Patent
Chu

(10) Patent No.: US 7,877,152 B2
(45) Date of Patent: Jan. 25, 2011

(54) BIPOLAR STIMULATION/RECORDING DEVICE WITH WIDELY SPACED ELECTRODES

(75) Inventor: Jennifer Chu, Haverford, PA (US)

(73) Assignee: JusJas LLC, Haverford, PA (US)

( * ) Notice: Subject to any disclaimer, the term of this patent is extended or adjusted under 35 U.S.C. 154(b) by 184 days.

(21) Appl. No.: 11/830,235

(22) Filed: Jul. 30, 2007

(65) Prior Publication Data

US 2008/0027508 A1 Jan. 31, 2008

Related U.S. Application Data

(60) Provisional application No. 60/834,184, filed on Jul. 31, 2006.

(51) Int. Cl.
*A61N 1/04* (2006.01)
(52) U.S. Cl. ...................................................... 607/145
(58) Field of Classification Search ................. 607/145, 607/148–150, 118, 139
See application file for complete search history.

(56) References Cited

U.S. PATENT DOCUMENTS

| | | | | |
|---|---|---|---|---|
| 1,487,998 A | * | 3/1924 | Woolf | 607/139 |
| 1,633,878 A | | 6/1927 | Wallerich | |
| 1,657,149 A | * | 1/1928 | Catlin | 607/139 |
| 1,746,379 A | * | 2/1930 | Campbell | 607/149 |
| 1,853,814 A | * | 4/1932 | Huth | 607/152 |
| 1,889,271 A | * | 11/1932 | Zerne | 607/152 |
| 2,404,283 A | | 7/1946 | Gieringer | |
| 3,620,219 A | * | 11/1971 | Barker | 607/139 |
| 4,180,079 A | | 12/1979 | Wing | |
| 4,276,879 A | | 7/1981 | Yiournas | |
| 4,613,328 A | | 9/1986 | Boyd | |
| 4,662,363 A | | 5/1987 | Romano et al. | |
| 4,758,227 A | | 7/1988 | Lancaster, Jr. et al. | |

(Continued)

FOREIGN PATENT DOCUMENTS

CA          675494       *    3/1963

(Continued)

OTHER PUBLICATIONS

Notification of Transmittal of the International Search Report and the Written Opinion of the International Searching Authority or the Declaration, mailed on Jun. 2, 2008 in corresponding International Application No. PCT/US07/17110, filed Jul. 31, 2007.

(Continued)

*Primary Examiner*—Scott M Getzow
*Assistant Examiner*—Amanda Patton
(74) *Attorney, Agent, or Firm*—Banner & Witcoff, Ltd

(57) ABSTRACT

A bipolar stimulator probe suitable for application of intramuscular stimulation provides an active stimulator electrode and a reference electrode as part of a single tool. The separation between the electrodes is significantly greater than the electrode separation of known bipolar stimulator probes and bipolar bar electrode configurations. The probe tool may be configured to permit adjustment of the fixed relative position of the electrodes within a given range. By providing a relatively wide spacing between the two electrodes, the tool can be used to approximate the effect of monopolar stimulation with a separate reference electrode, with the electrical stimulus producing less pain to the patient compared to bipolar stimulation where the two electrodes are spaced apart by only 2-4 cm or less.

15 Claims, 3 Drawing Sheets

U.S. PATENT DOCUMENTS

| | | | |
|---|---|---|---|
| 4,878,493 A * | 11/1989 | Pasternak et al. | 607/99 |
| 5,199,952 A | 4/1993 | Marshall, Sr. et al. | |
| 5,211,175 A | 5/1993 | Gleason et al. | |
| 5,535,746 A | 7/1996 | Hoover et al. | |
| 5,735,868 A | 4/1998 | Lee | |
| 5,810,762 A | 9/1998 | Hofmann | |
| 5,922,012 A | 7/1999 | Sakano | |
| 5,968,063 A | 10/1999 | Chu et al. | |
| 6,006,130 A * | 12/1999 | Higo et al. | 604/20 |
| 6,058,938 A | 5/2000 | Chu et al. | |
| 6,175,764 B1 | 1/2001 | Loeb et al. | |
| 6,181,965 B1 | 1/2001 | Loeb et al. | |
| 6,308,104 B1 * | 10/2001 | Taylor et al. | 607/118 |
| 6,532,390 B1 | 3/2003 | Chu et al. | |
| 6,546,290 B1 | 4/2003 | Shloznikov | |
| 6,928,319 B2 * | 8/2005 | Wang | 607/2 |
| 7,181,288 B1 * | 2/2007 | Rezai et al. | 607/116 |
| 2002/0188332 A1 | 12/2002 | Lurie et al. | |

FOREIGN PATENT DOCUMENTS

WO     02/089903     11/2002

OTHER PUBLICATIONS

C. Chan Gunn, M.D., "The Gunn Approach to the Treatment of Chronic Pain: Intramuscular Stimulation for Myofascial Pain of Radiculopathic Origin", (2d ed.), 1996.

Ghoname EA. Craig WF. White PF. Ahmed HE. Hamza MA. Henderson BN. Gajraj NM. Huber PJ. Gatchel RJ. Percutaneous Electrical Nerve Stimulation for Low Back Pain: A Randomized Crossover Study. JAMA. 281(9):818-23, Mar. 3, 1999.

Yokoyama M. Sun X. Oku S. Taga N. Sato K. Mizobuchi S. Takahashi T. Morita K. Comparison of Percutaneous Electrical Nerve Stimulation with Transcutaneous Electrical Nerve Stimulation for Long-term Pain Relief in Patients with Chronic Low Back Pain. *Anesthesia & Analgesia*. 98(6):1552-6, Jun. 2004.

Minder PM. Noble JG. Alves-Guerreiro J. Hill ID. Lowe AS. Walsh DM. Baxter GD. Interferential therapy: lack of effect upon experimentally induced delayed onset muscle soreness. *Clinical Physiology & Functional Imaging*. 22(5):339-47, Sep. 2002.

Werners R., Pynsent PB., Bulstrode CJ: Randomized Trial Comparing Interferential Therapy with Motorized Lumbar Traction and Massage in the Management of Low Back Pain in a Primary Care Setting. *Spine*. 24(15):1579-84, Aug. 1, 1999.

Popovic M.R. Keller T. Modular transcutaneous functional electrical stimulation system. [Case Reports. Journal Article] *Medical Engineering & Physics*. 27(1):81-92, Jan. 2005.

Koke A.J. Schouten JS. Lamerichs-Geelen MJ. Lipsch JS. Waltje Em. van Kleef M. Patijn J. Pain reducing effect of three types of transcutaneous electrical nerve stimulation in patients with chronic pain: a randomized crossover trial. *Pain*. 108(12):36-42, Mar. 2004.

Chu J: Twitch Response in Myofascial Trigger Points. J Musculoske Pain 6(4), 99-110, 1998.

Chu J: Twitch-obtaining intramuscular stimulation (TOIMS) in acute partial radial nerve palsy. Electromyogr Clin Neurophysiol 39:221-226, 1999.

Chu J: The role of the monopolar electromyographic pin in myofascial pain therapy: automated twitch-obtaining intramuscular stimulation (ATOIMS$^{sm}$) and electrical twitch-obtaining intramuscular stimulation (ETOIMS$^{sm}$)- Electromyogr Clin Neurophysiol 39: 503-511, 1999.

Chu J: Twitch-Obtaining Intramuscular Stimulation: Observations in the Management of Radiculopathic Chronic Low Back Pain. J Musculoske Pain 7(4): 131-146, 1999.

Chu J: Twitch obtaining intramuscular stimulation (TOIMS): Long-term observations in the management of chronic partial cervical radiculopathy. Electromyogr Clin Neurophysiol 40:503-510, 2000.

Gozon B, Chu J, Schwartz I: Lumbosacral radiculopathic pain presenting as groin and scrotal pain: Pain management with twitch-obtaining intramuscular stimulation. A case report and review of literature. Electromyogr Clin Neurophysiol 41:315-318, 2001.

Chu J, Gozon B, Schwartz I: Twitch-Obtaining Intramuscular Stimulation in Reflex Sympathetic Dystrophy. Electromyogr Clin Neurophysiol 42:259-22, 2002.

Chu J: The muscle twitch in myofascial pain relief: effects of acupuncture and other needling methods. Electromyogr Clin Neurophysiol 42:307-311, 2002.

Chu J: The local mechanism of Acupuncture. Chinese Medical Journal (Taipei) 65:299-302 2002.

Chu J, Neuhauser D, Schwartz I, Aye HH: The efficacy of automated/ electrical twitch obtaining intramuscular stimulation (ATOIMS/ ETOIMS) for chronic pain control : Evaluation with statistical process control methods. Electromyogr clin Neurophysiol 42:393-401, 2002.

Chu J, Yuen KF Wang BH, Chan RC, Schwartz I, Neuhauser D: Electrical Twitch-Obtaining Intramuscular Stimulation in Lower Back Pain: A Pilot Study. Am J Phys Med Rehabil 83, No. 2: 104-111, 2004.

Chu J et al: Efficacy of Electrical Twitch Obtaining Intramuscular Stimulation (ETOIMS) in Chronic Neck Pain (CNP). (abstract accepted for presentation at American Academy of Physical Medicine and Rehabilitation, Oct. 2005.

Chu J et al: Efficacy of Electrical Twitch Obtaining Intramuscular Stimulation (ETOIMS) in Chronic Lower Back Pain (CLBP). (abstract accepted for presentation at American Academy of Physical Medicine and Rehabilitation, Oct. 2005.

Chu, J., "Dry Needling (Intramuscular Stimulation) in Myofascial Pain Related to Lumbosacral Radiculopathy", Eur. J. Phys. Med. Rehabil. 1995: 5 No. 4, pp. 106-120.

Chu, J., "Comment on the Simmons Literature Review Column, 'Myofascial Pain Syndrome—Trigger Points', "J. Musculoskeletal Pain, vol. 5(1) 1997, pp. 133-135.

Photographs of IMS device purchased from Mr. Young H. Lee in Feb. 1996.

C.C. Gunn, et al., "Dry Needling of Muscle Motor Points for Chronic Low-Back Pain: A Randomized Clinical Trial With Long Term Follow-Up", Spine, vol. 5, No. 3, May/Jun. 1980, pp. 279-291.

C Chan Gunn, "Treating Myofascial Pain: Intramuscular Stimulation (IMS) for Myofascial Pain Syndromes of Neuropath Origin", 1989.

Open Letter re IMS treatment offered by Jennifer Chu,M.D., University of Pennsylvania Medical Center, Mar. 13, 1996.

"Patient Information on Intramusclular Stimulation (IMS) for Management of SoftTissue/Neuropathic Pain", University of Pennsylvania Medical Center, Apr. 8, 1996.

Travell, J.G., Simons, D.G., "Myofascial Pain and Dysfunction: The Trigger Point Manual", vol. 1. Williams and Wilkins, Baltimore, 1983, Table of Contents, Preface, Chapter 3 "Apropos of all Muscles".

Travell, J.G., Simons, D.G., "Myofascial Pain and Dysfunction: The Trigger Point Manual", vol. 2. The Lower Extremities. Williams and Wilkins, Baltimore, 1992, Table of Contents, Chapter 2 "General Issues".

Stålberg, E., Trontelj, J., "Single Fiber Electromyography, Studies in Healthy and Diseased Muscle", 2d Ed., Raven Press Ltd., New York (1994).

Chu, J. "Does EMG (dry needling) reduce myofacial pain symptoms due to cervical nerve root irritation?" Electromyogr. clin. Neurophysiol., 37:259-272, 1997.

Chu, J. "Twitch-Obtaining Intramuscular Stimulation: Its Effectiveness in The Long-Term Treatment of Myofascial Pain Related to Lumbosacral Radiculopathy", Arch. Phys. Med. Rehabil., 78:1024, Sep. 1997 (abstract).

Chu, J. "Twitch-Obtaining Intramuscular Stimulation: Effective for Long-Term Treatment Myofascial Pain Related to Cervical Radiculopathy", Arch. Phys. Med. Rehabil., 78:1042, Sep. 1997 (abstract).

The NeuroControl Stlm™ System Clinician Manual, Doc. # 265-1005-P, Neuro Control Corp., 1999-2000.

Supplementary European Search Report dated Jul. 6, 2009 in corresponding EP Application No. 07836368.6.

Examination Report dated Jul. 26, 2010 in related NZ application No. 574624, national phase of corresponding PCT application PCT/ US07/17110.

* cited by examiner

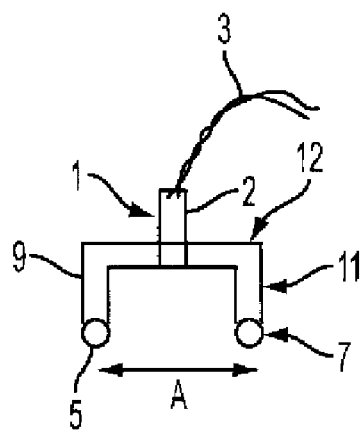
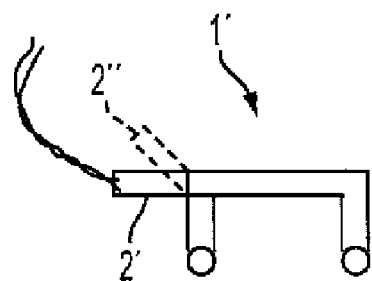
FIG. 1          FIG. 1a
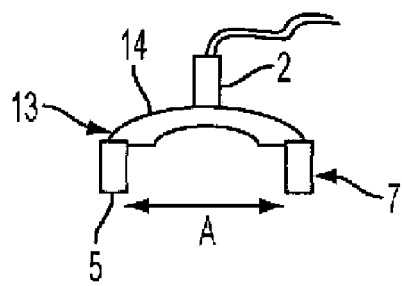
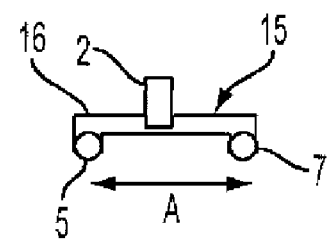
FIG. 2          FIG. 3
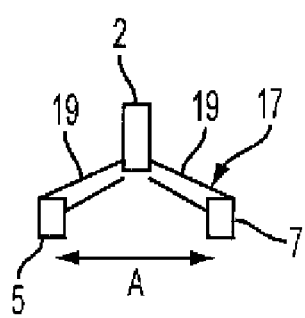
FIG. 4

BIPOLAR STIMULATION/RECORDING DEVICE WITH WIDELY SPACED ELECTRODES

This application claims the benefit of prior co-pending U.S. provisional application Ser. No. 60/834,184, filed Jul. 31, 2006.

BACKGROUND OF THE INVENTION

Bipolar stimulator probes attachable to an electrical stimulator device or an electromyographic (EMG) device are commercially available for surface stimulation of peripheral nerves. Such apparatus provide both a stimulation electrode and a reference electrode on a single device. There are also bipolar bar electrode configurations, and sets of separate (individual) electrodes, for surface recording of nerve and muscle action potentials, and that can also serve to provide electrical muscle stimulation.

These types of devices can be used in surface stimulation for eliciting muscle twitches of the type sought in a muscle pain and discomfort relieving method developed by the present inventor, referenced herein as Surface Applied Electrical Twitch Obtaining Intramuscular Stimulation (SA-ETOIMS™). This methodology is described in U.S. provisional patent application Ser. No. 60/715,137, entitled "Intramuscular Stimulation Therapy Using Surface-Applied Localized Electrical Stimulation," filed Sep. 9, 2005, and corresponding regular U.S. patent application Ser. No. 11/470,757, filed Sep. 7, 2006, which are hereby incorporated by reference in their entireties. This technique involves the provision of brief electrical stimulation at multiple motor end-plate zones (twitch-points) in many muscles. It is important that the stimulation method be "user friendly," to both patient and treating clinician. That is, the stimulation should not cause significant additional discomfort to the patient and the method should be easy to apply for the clinician.

Commercially available standard bipolar stimulating probes have an inter-probe distance of 2 cm or less between the active and reference electrodes. This type of bipolar stimulation induces significant stimulation pain making it undesirable for use in the SA-ETOIMS™ procedure. In addition, due to the close proximity of the active and reference electrodes, twitches that may be elicited with such devices are small and have low forces, and therefore do not provide significant pain relieving effects. Similarly, as mentioned, surface electrodes that can be used for recording as well as stimulation purposes are available in the form of a bar electrode pair. Such devices have an inter-electrode distance of about 3-4 cm, and thus the same problem of inducing stimulation pain arises if these devices are used to perform SA-ETOIMS™. Stimulation/recording electrodes are also available as separate (individual) electrodes. However, separate individual electrodes are less than ideal for use in the SA-ETOIMS™ procedure, since both the active and reference electrodes have to be moved in bi-manual fashion to multiple stimulus and reference sites, thus slowing down and encumbering the SA-ETOIMS™ procedure and making the procedure more difficult for the clinician. These difficulties are alleviated to some extent by use of a monopolar stimulation tool, as is explained below.

The present inventor has performed SA-ETOIMS™ using monopolar stimulation, that is, with a generally pen-like tool having a single electrode mounted on its tip, which is used in conjunction with a separate reference electrode. Providing the stimulation electrode in the form of a stiff, pen-like tool gives the clinician a firm place to hold the tool in order to easily move the electrode to different stimulation sites in a rapid and efficient manner. The pain or discomfort relieving therapeutic effects are substantially achieved only when such sites with large force twitches are stimulated. SA-ETOIMS is performed in a time-based fashion, i.e. in incremental treatment segments of 10-15 minutes sessions to one hour sessions. For therapeutic effects to be substantial, it is essential that many large force twitch sites be sought, located and treated within the limits of timed sessions which are affordable and paid for by the patient as fee-for-service performed. To be able to search for as many large force twitch sites as possible within a given time-frame, the electrode needs to be moved to another site as soon as the twitch is elicited, i.e., within a fraction of a second. Therefore, it is crucial that the stimulation probes and reference electrodes allow expedient performance of the SA-ETOIMS procedure. However, a stimulation electrode provided in the form of a known-type adhesively applied disposable electrode has no firm place for the clinician to hold onto effectively, and is also impractical for efficient use in a treatment method involving electrode relocation every fraction of a second. The monopolar stimulation probe, similar in size and length to that of a pen, is very useful in SA-ETOIMS procedure and can be easily applied onto the skin surface for stimulation to evoke muscle twitches and to facilitate the search for large force twitch sites. However, the monopolar stimulation method requires use of a separate remote surface reference electrode, which is typically a known-type adhesively applied disposable electrode. The treatment is less painful than with bipolar stimulation with electrodes that are spaced 2-4 cm or less apart. However, monopolar stimulation has disadvantages.

With monopolar stimulation, moving the stimulating probe to different stimulus points has to be accompanied by relocating the disposable separate reference electrode to different body sites, multiple times, to avoid repetitive unnecessary stimulation and induced pain at the reference site. This type of surface reference electrode is not conducive to rapid movements, e.g., every second. Therefore, in practice, the electrode is moved after every minute or so. This bimanual work wastes time for the treating clinician since the disposable reference electrode will lose its adhesiveness, dislodge and/or fall off when subjected to multiple re-positioning and re-application onto the skin surface.

To avoid skin irritation from repetitive stimulation at one reference site only, and to avoid having to often move the single, separate reference electrode from place to place, several reference electrodes can be placed at different sites on the skin. By rotating the activation of different reference electrodes, there is better and more even distribution of the stimulus to different reference sites. This reduces the number of times any single reference electrode is subjected to removal and relocation. However, to activate a reference electrode placed at a different site, the clinician has to detach an alligator clip from the first reference electrode and re-attach it onto the next reference electrode with one hand, since the other hand holds onto the monopolar probe used for treatment. This creates inconvenience for the clinician since the alligator clip might not attach well when performed singlehandedly. If bimanual attachment is required, it is disruptive to the treatment. It is also cumbersome since the multiple electrodes still need to be physically removed and rotated for placement at other skin sites to avoid discomfort at sites that have undergone previous repetitive stimulation. In prolonged treatments necessitating multiple different site placements of the reference electrodes, the electrodes can eventually lose their adhesiveness also causing them to fall off the skin surface. Additionally, when the reference electrode does not stick properly to the skin, the reduction in contact area of the reference electrode to the skin induces more treatment pain.

For optimal pain relieving results with SA-ETOIMS™, it is desirable to search for as many muscle motor points that can produce large force twitches as quickly as possible in a time-based treatment. Stimulation can be enhanced, and the yield of large force twitches made easier, when the surface reference electrode is placed at a distance from the stimulating probe. If the reference electrode is placed close to the stimulating probe, the treatment is painful and the twitches are small. The further the reference electrode is placed away from the stimulating probe, e.g., by as much 2-3 feet, the easier it is to elicit the sought-after large force twitches from deeply situated motor end plate zones (twitch-points). As one example, the reference electrode can be on the mid or low back region while stimulating calf muscles or arm muscles, but this creates a problem for the clinician if the reference electrode is at a site not within easy reach. The clinician then has to temporarily stop the treatment every time he/she has to reach over to the reference electrode or has to move closer to re-position the remote reference electrode to another location within reach.

Additional disadvantages of the monopolar stimulation approach (with separate reference electrode) include the fact that the lengthy separated wires of the stimulating and reference electrodes tend to get tangled, requiring that the clinician stop the treatment to untangle the wires. Additionally, there is a difficulty in finding a suitable site for reference electrode placement on the ventral (front) surface of the body where the skin is more sensitive to electrical stimulation, especially those associated with repetitive stimulation to one site. Also, if the clinician forgets to remove the reference electrode from the back of the body while treating muscles on the front of the body or the chest, a trans-thoracic current may be induced and adversely affect heart rhythm.

SUMMARY OF THE INVENTION

With the foregoing in mind, the present inventor recognized that there is a need for a bipolar stimulator probe, wherein the active stimulator electrode and the reference electrode are provided as part of a single tool, and the separation between the electrodes is fixable at a set, e.g., standardized, distance which is significantly greater than the electrode separation of known bipolar stimulator probes and bipolar bar electrode configurations. As a general principle, to obtain large force twitches and to simulate the monopolar stimulating condition with the bipolar tool, the distance between the active and reference electrodes should be spaced far apart as possible. Ideally, the two electrodes could be spaced as far apart as possible (perhaps by 2-3 feet or more), but it may not be clinically practical to have this type of very wide spacing provided by a bipolar electrode tool. Such a device may be too heavy, bulky, and /or awkward for practical use. Also, the uneven contours of the intervening tissues may prevent the reference electrode from touching the skin surface. For practical utility, an electrode spacing of 15-16 cm (6 inches) may be provided between the stimulating and reference electrodes. However, it is advantageous to have an option for increasing or decreasing the spacing between the two electrodes. The probe tool may be configured to permit adjustment of the fixed relative position of the electrodes within a given range, such as by slideable or otherwise movably mounted electrodes similar to the principle used in a sliding gauge such as a Vernier caliper. A bipolar probe tool providing a wide spacing between the two electrodes will approximate the effect of monopolar stimulation with a separate reference electrode, with the electrical stimulus producing less pain to the patient compared to bipolar stimulation where the two electrodes are spaced apart by only 2-4 cm or less. The ability to reduce the inter-electrode distance is essential for treating small muscles in the face, hands and feet.

BRIEF DESCRIPTION OF THE DRAWINGS

FIG. 1 is a diagrammatic depiction of a bipolar stimulation probe in accordance with the invention.

FIG. 1a is a diagrammatic depiction of a variation on the FIG. 1 embodiment, with the handle moved to one end of the tool (Vernier caliper-style).

FIG. 2 is a diagrammatic depiction of a further bipolar embodiment stimulation probe tool.

FIG. 3 is a diagrammatic depiction of a further exemplary probe tool in accordance with the invention.

FIG. 4 is a diagrammatic depiction of yet another exemplary probe tool embodiment.

DETAILED DESCRIPTION OF EXEMPLARY EMBODIMENTS

Figure 5:
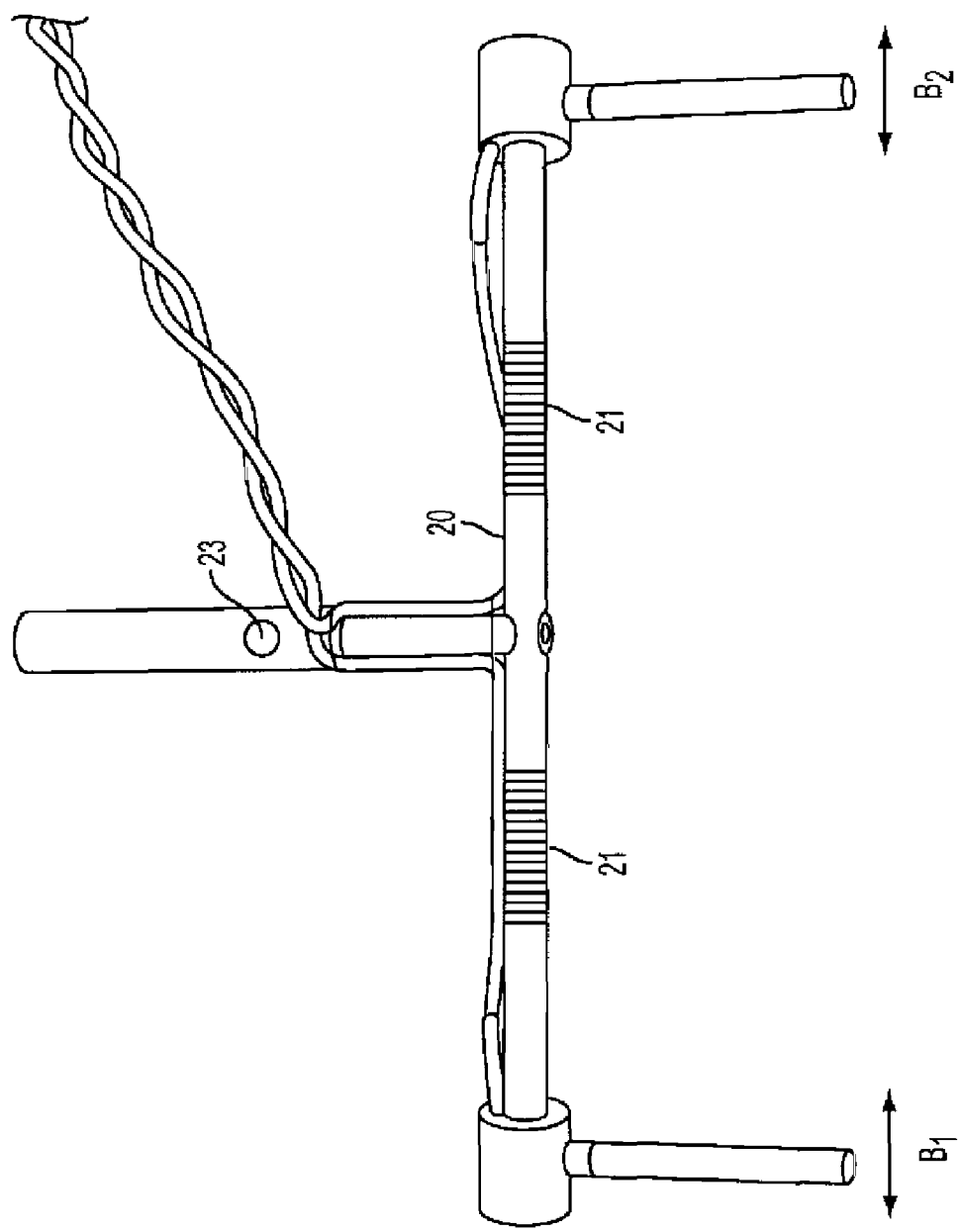
FIG. 5 is a perspective view depicting a prototype probe tool in accordance with the invention, corresponding to the diagrammatic representation of FIG. 1.

Referring now to the appended drawings, FIG. 1 is a diagrammatic depiction of a bipolar stimulation probe 1 in accordance with the invention. Handle 2 is preferably about 3-6" or so in length. Wires 3 lead to the two spaced electrodes 5, 7 of the probe tool, and connect to a suitable stimulator/recording device, such as the commercially available electrical stimulation unit, Model DS 7, from Digitimer Limited (Herforthshire, England). As illustrated, electrode 5 may be the stimulating electrode, and electrode 7 may be the reference electrode. Electrodes 5, 7 are mounted on the ends of spaced arms or prongs 9, 11, attached to each other by a connection cross member 12, which may extend between the stimulating prongs 9, 11 at right angles to the prongs, as shown in FIG. 1. Prongs 9, 11 preferably have a length of about 2.5" (50 mm) and are spaced from each other to provide a separation of distance "A" between electrodes 5 and 7, which is preferably at least 6" center to center, and with an upper limit of 24-36". Electrodes 5, 7 may be of a known type. For stimulation applications, the electrodes may be covered by a wad of wet cotton or wool soaked in water, but it is preferable to use hypertonic 9-10% saline to facilitate electrical conduction. The stimulating electrodes can be provided in the form of disposable felt pads manufactured for SA-ETOIMS. They can be pre-packaged already pre-soaked or immersed in hypertonic 9-10% saline to facilitate use in treatment. For recording purposes, the recording surface is made preferably with stainless steel or another known conductive metallic surface of suitable type.

A trigger button may be mounted on probe tool 1, to permit a clinician to conveniently activate the probe for stimulation applications. The switch is preferably touch-sensitive, activated by a pressure on the patient contact surface of the stimulating electrode or activated by a push-button on the handle, on its side or end, for on/off control triggered by the clinician. The probe may also be activated via a separate hand button that can be triggered by the patient or another person.

The stimulating probe should be light-weight, preferably weighing about 2-4 oz or less, e.g., preferably the approximate weight of a writing pen. However, the materials used for the connection cross member 12 should be sturdy enough to withstand breakage upon being subjected to repetitive use and receiving significant impacting forces along the attached prongs from the forceful twitches. The circumference of the handle or stem 2 of probe 1 is preferably about 4 cm, or on the order of the diameter of a writing pen, for ease of grasp and comfort for the clinician. Handle 2 preferably has a length of 3-6 inches to avoid wobbling of the electrodes on the surface of the skin by virtue of hand movements. Alternatively, instead of a stem-like handle, the connection cross member 12 may also be of a thickness that can allow it to be used as a handle in the same fashion commonly in use with steam irons (see FIG. 2, discussed below). Also, the handle may be placed at one end of the connection cross member 12, similar to the handle of a Vernier caliper. This is illustrated in FIG. 1*a*, wherein the tool has a repositioned handle 2'. In such a design, the handle may be tilted up at an obtuse angle relative to the connection cross member 12 (as commonly seen in the handle of a frying pan or sauce pan), such that the handle will, in use, avoid touching the patient's skin and muscle tissue. Such a handle is shown in dotted lines in FIG. 1*a* (labeled 2"). The handle should be of a girth comfortable for gripping for long periods of time. The control for changing the inter-electrode distance can be suitably placed on the handle for thumb manipulation. The control may be a wheel or button that can also lock-in the chosen inter-electrode distance. Both electrode surfaces in contact with the patient will preferably be circular in shape and have a diameter of 1-2 cm.

FIG. 2 is a diagrammatic depiction of a further embodiment, probe tool 13, wherein the spaced electrode mounting structure is provided in the form of an arched/semi-lunar shaped arm 14, with the active and reference electrodes 5, 7 mounted on the ends, e.g., with a spacing "A" of about 6". This embodiment also has a handle 2, as in the first embodiment, which attaches to a central portion of arm 14. Stem-like handle 2 may be omitted, in which case the arched/semi-lunar shaped arm 14 can be used as the handle with a girth comfortable for prolonged gripping, similar to that of a steam iron.

On uneven body regions, the stimulation and reference electrodes may not be able to easily reach to touch the skin surface simultaneously. Simply re-positioning the stimulating electrode in treating these areas can overcome this difficulty. Also, fashioning the connector piece between the active and reference electrodes to be in the shape of an arc or semi-lunar shape, as shown in FIG. 2, will help with this issue, by fitting better over the contour of a muscle. Also, the probe arms could be made movable or bendable to permit the probe ends to reach to touch the skin surface. This concept is similar to that of the flexible stem of a reading lamp that can be bent to supply the optimal angle for providing the correct amount of light for reading. The probe device arms and handle should be made of, or shielded by, plastic or other insulative material to electrically isolate the stimulation and reference electrodes and prevent a short of the electrodes or electrical impulses passing to the clinician.

FIG. 3 is a diagrammatic depiction of a further exemplary embodiment, probe tool 15, wherein the spaced electrode mounting structure is provided in the form of an essentially flat bar 16, to which the active and reference electrodes 5, 7 may be mounted, directly, or in very short arms or prongs, e.g., with an arm length of 0.5" or less, and an inter-electrode spacing of about 6". This embodiment also has a handle 2, as in the first embodiment, which attaches to a central portion of flat bar 15. This type of bar electrode is more suitable for recording or stimulation purposes over flat and even surfaces. Probe tool 15 is not so well suited for use where there is a need for rapid search and location of large force twitch sites in performing SA-ETOIMS therapy. This is due to the short length of the prongs of the bar electrode that interfere with placement of both electrodes in contact with the skin surface over contoured muscles.

FIG. 4 is a diagrammatic depiction of yet another exemplary embodiment, probe tool 17, wherein the spaced electrode mounting structure is provided in the form of a pair of arms 19 which converge to form an obtuse angle. Similar to the previous embodiments, the active and reference electrodes 5, 7 may be mounted on the end of the arms, e.g., with an inter-electrode spacing of about 6". This embodiment also has a handle 2, as in the first embodiment, which in this case attaches to the central apex portion of the structure formed by the angled (converging) arms 19.

SA-ETOIMS™ related advantages potentially realizable a wide-spaced bipolar probe tool in accordance with the invention are described below.

The bipolar probe tool allows SA-ETOIMS™ treatment to be performed faster since bi-manual work is not required of the clinician as with the monopolar stimulation method that requires moving the stimulating electrode, in addition to the separate time and attention required to move the reference probe during the treatment procedure.

The paired movement of the reference electrode together with the active stimulating probe prevents any one site over which the reference has been placed, from prolonged excessive stimulation and unnecessary discomfort to the patient.

Having a fixed or limited adjustable distance between the stimulator and the reference electrodes allows the reference electrode to be in the same area of the muscle treated and the stimulus is localized to the one muscle of interest. This stimulus isolation to one muscle is possible in treating large muscles of the buttock and lower limbs. The stimulus can also be isolated to one side of the body since both stimulus and reference electrodes can be moved together for performing such purposes. This substantially eliminates the possibility of accidental placement of the reference electrode on the back of the body while treating muscles on the front of the body, and the attendant risk of inducing trans-thoracic current that can interfere with heart rhythm.

With the bipolar probe tool, there need only be one cable leading to the stem of the tool, making the tool more user friendly by avoiding the need for two separate wires extending to separate reference and stimulator electrodes. This avoids the entanglement of wires during treatment and leads to better utilization of treatment time.

Figure 6:
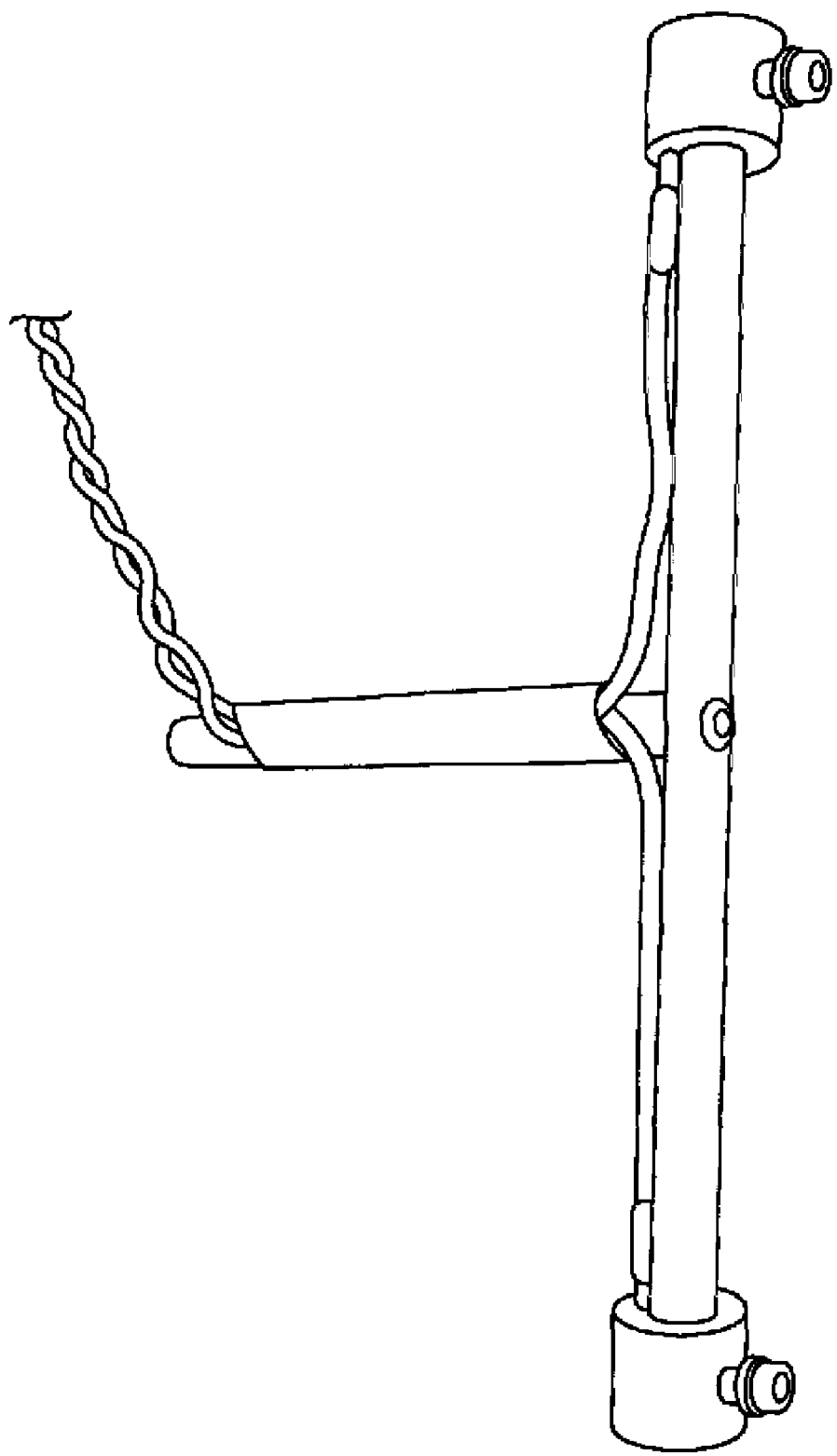
FIG. 6 is a perspective view of another prototype probe tool in accordance with the invention, corresponding to the diagrammatic depiction of FIG. 3.

The present inventor has used prototype probes similar to those depicted in FIGS. 5 and 6 to provide SA-ETOIMS treatments with a fixed interelectrode distance of 15-16 cm or 6" and found the electrode spacing to be sufficient to allow large force twitches to be elicited. The treatments with such a probe is faster, more efficient and decidedly less painful at the reference site compared to monopolar stimulation using static reference electrode placement. With certain muscles, such as the buttocks of overweight patients, in certain instances, this spacing may not be sufficient to elicit large force twitches. This situation can be overcome by a slideable or otherwise moveable mechanism to increase the distance between the active and reference electrodes to more than 6" and possibly up to 24"-36", or more. Such an arrangement can be used to facilitate the positioning of the bipolar probe such that the active stimulation electrode is positioned on the muscle of interest, and the reference electrode is positioned to lie on a different muscle. This advantageously simulates monopolar stimulation conditions to a great extent, due to the wide spacing distance between the two electrodes. A slidable movement of the electrodes along the cross-arm 20, to adjust the electrode spacing, is diagrammatically depicted by arrows $B_1$ and $B_2$ in FIG. 5. Flexible joints, allowing the cross-arm 20 to bend in order to reposition/reorient the electrodes, are diagrammatically depicted at 21. Also depicted in FIG. 5 is a handle-mounted user activated push-button 23 that may be associated with a trigger switch of the tool, as previously described. (The illustrated slidable movement, flexible joints and push-button are optional features not present in the prototype probes used by the inventor.)

The bipolar probe devices of the present invention also have utility beyond their advantageous use for SA-ETOIMS™ stimulation purposes. Such devices can also be used for other stimulation procedures, wherein it may be necessary or desirable for the reference and active electrodes to be widely spaced apart, or in situations wherein it is desired to simulate monopolar stimulation conditions for stimulating nerve and/or muscle.

This same type of probe can also be used for recording compound muscle action potentials and sensory nerve action potentials for performing nerve conduction study (NCS) recordings, using an electromyographic (EMG) machine. For motor nerve conduction studies with recording from large muscles, the active electrode is placed over the motor point of the muscle of interest and the reference electrode is placed over the tendon of the recorded muscle or in an electrically inactive region such as the bone on which the tendon of interest inserts. Similarly, for recording sensory nerve action potentials, the active and reference electrodes are placed over the line of distribution of the sensory nerve.

In order to obtain better electrical readings for recording procedures, the probe electrodes that are placed in contact with the patient's skin are preferably made of metal or other disposable metallic conducting material, such as those routinely used in electrocardiographic (EKG) and nerve conduction study (NCS) recordings, instead of the disposable wet felt pads that are preferably used for stimulating purposes. The active and reference leads of the tool will preferably be of a compatible type that can fit into the appropriate receptacles of the pre-amplifier of the EMG machine. The spaced electrode pairing provided by the present invention is useful in facilitating the search for the best motor point from which to record for a given muscle. This is due to the ease in repositioning the recording and reference electrodes, and the use of a fixable or standardized distance between the two electrodes. When the spacing between the active and reference electrodes is not held constant (fixed), the shape and amplitude of the recorded potential changes in relationship to the distance between these two electrodes; this variability is especially notable with sensory nerve action potentials recordings. The bar electrode style probe as shown in FIG. 3, is suitable for recording of sensory and muscle action potentials.

It will be understood that while the invention has been described in conjunction with various embodiments and details thereof, the foregoing description and examples are intended to illustrate, but not limit the scope of the invention. Numerous other variations and arrangements are within the scope of the invention.

The invention claimed is:

1. A bipolar stimulator probe comprising an active stimulator electrode with a first skin contact surface, a second electrode with a second skin contact surface, serving as a reference electrode to said active stimulator electrode, and a user handle provided as part of a single tool, wherein the probe tool comprises a spaced electrode mounting structure fixing the positions of the electrodes with respect to each other during skin contact, and during movement of the probe from one skin contacting position to another, and providing for guided adjustment of the fixed relative positions of the electrodes within a given range, wherein the spaced electrode mounting structure comprises a pair of spaced arm portions, said first and second skin contact surfaces being presented at free ends of said arm portions, and having at least central portions thereof situated proximally within a common plane and facing from said free ends in respective directions which are unopposed to each other, said guided adjustment of the fixed relative positions of the electrodes being proximally within said common plane.

2. The bipolar stimulator probe according to claim 1, wherein at least one of the electrodes is slideably mounted by the spaced electrode mounting structure to permit adjustment of a fixed position thereof.

3. The bipolar stimulator probe according to claim 1, wherein the spaced electrode mounting structure is movable or bendable to permit adjustment of the fixed relative positions of the active and reference electrodes in order to reach to touch uneven skin surfaces.

4. The bipolar stimulator probe according to claim 1, wherein the spaced electrode mounting structure further comprises a connection member extending cross-wise between the arms.

5. The bipolar stimulator probe according to claim 4, wherein at least one of said electrodes is slidably mounted on said connection member to permit adjustment of a fixed position thereof.

6. The bipolar stimulator probe according to claim 4, wherein said user handle extends from an end of said connection member, away from said spaced arms.

7. The bipolar stimulator probe according to claim 4, wherein said arms extend at right angles to said connection member.

8. The bipolar stimulator probe according to claim 4, wherein said arms comprise an electrically insulative material arranged to electrically isolate said active and reference electrodes.

9. The bipolar stimulator probe according to claim 1, further comprising a trigger switch to permit a user to conveniently electrically activate the probe for stimulation applications.

10. The bipolar stimulator probe according to claim 9, wherein the trigger switch is activated by a push-button provided on the handle.

11. The bipolar stimulator probe according to claim 1, wherein said electrodes are circular in shape.

12. The bipolar stimulator probe according to claim 11, wherein said electrodes have a diameter in the range of 1-2 cm.

13. The bipolar stimulator probe according to claim 1, wherein each of said active stimulator electrode and reference electrode comprises a covering of porous liquid absorbent material selected from the group consisting of: cotton, felt and wool.

14. The bipolar stimulator probe according to claim 13, wherein said porous liquid absorptive material comprises cotton material.

15. The bipolar stimulator probe according to claim 13, wherein said porous liquid absorptive material comprises a felt pad.

* * * * *